United States Patent
Wadell et al.

(10) Patent No.: US 7,528,113 B2
(45) Date of Patent: May 5, 2009

(54) METHOD AND COMPOSITION FOR THE TREATMENT OF ADENOVIRAL OCULAR INFECTIONS

(75) Inventors: Goran Wadell, Umea (SE); Niklas Arnberg, Umea (SE)

(73) Assignee: Adenovir Pharma AB, Helsingborg (SE)

( * ) Notice: Subject to any disclaimer, the term of this patent is extended or adjusted under 35 U.S.C. 154(b) by 126 days.

(21) Appl. No.: 10/997,955

(22) Filed: Nov. 29, 2004

(65) Prior Publication Data

US 2005/0080041 A1    Apr. 14, 2005

Related U.S. Application Data

(62) Division of application No. 10/130,979, filed as application No. PCT/SE00/02313 on Nov. 23, 2000, now abandoned.

(30) Foreign Application Priority Data

Nov. 26, 1999    (SE) .................................... 9904289

(51) Int. Cl.
*A61K 31/1008*    (2006.01)
*A61K 31/7012*    (2006.01)
*A61K 31/7016*    (2006.01)
*A61K 31/702*     (2006.01)
*C07H 5/04*       (2006.01)
*C07H 5/06*       (2006.01)
*C08B 37/00*      (2006.01)

(52) U.S. Cl. .............................. 514/23; 514/53; 514/61; 536/18.7; 536/55; 536/55.1; 536/55.2

(58) Field of Classification Search .................... 514/61
See application file for complete search history.

(56) References Cited

U.S. PATENT DOCUMENTS

| | | | |
|---|---|---|---|
| 4,522,803 A | 6/1985 | Lenk et al. | |
| 5,645,830 A | 7/1997 | Reid et al. | |
| 5,719,020 A * | 2/1998 | Liav et al. ...................... | 435/5 |
| 5,792,842 A * | 8/1998 | Iida et al. .................... | 536/17.2 |
| 5,858,698 A | 1/1999 | Armstrong et al. | |
| 6,235,313 B1 | 5/2001 | Mathiowitz et al. | |
| 2005/0201952 A1* | 9/2005 | Sharma ....................... | 424/48 |

FOREIGN PATENT DOCUMENTS

| | | |
|---|---|---|
| DE | 195 47 972 | 7/1997 |
| EP | 0 502 550 | 9/1992 |
| ES | 2 127 110 | 4/1999 |
| WO | 95/34595 | 12/1995 |
| WO | 97/29763 | 8/1997 |
| WO | 98/48817 | 11/1998 |
| WO | 00/48624 | 8/2000 |

OTHER PUBLICATIONS

2006 Chemical Abstracts Catalog, published by Chemical Abstracts Service, p. 52.*
Ajisaka et al., "Regioselective transglycosylation in the synthesis of oligosaccharides," Carbohyd. Res., (1994), vol. 259, pp. 103-115.
S. M. Arcasoy et al., "MUC1 and Other Sialoglycoconjugates inhibit Adenovirus-mediated Gene Transfer to Epithelial Cells," Am. J. Respir. Cell Mol. Biol., vol. 17, No. 4, pp. 422-435, (1997).

* cited by examiner

*Primary Examiner*—Shaojia Anna Jiang
*Assistant Examiner*—Eric S Olson
(74) *Attorney, Agent, or Firm*—Young & Thompson

(57) ABSTRACT

Adenoviral infections and in particular ocular adenoviral infections, e.g. keratoconjunctivitis, can be treated or alleviated by the administration of a substance, interfering with the interaction between the virus and the sialic acid receptor, in a therapeutically effective amount.

18 Claims, 3 Drawing Sheets

METHOD AND COMPOSITION FOR THE TREATMENT OF ADENOVIRAL OCULAR INFECTIONS

CROSS REFERENCE TO RELATED APPLICATION

Figure 1:
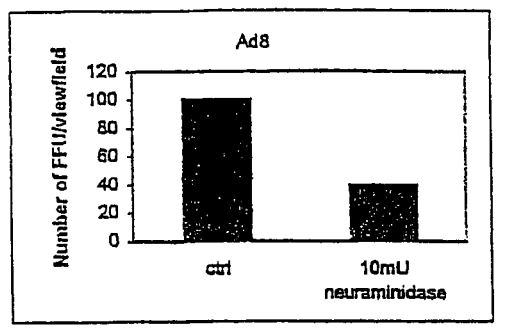
Figure 1:
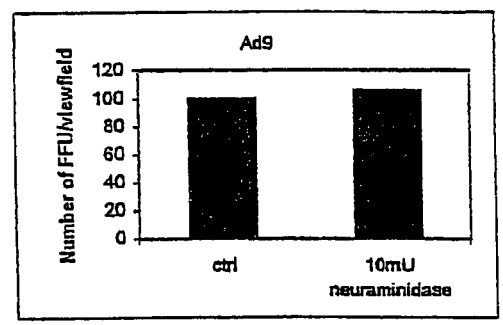
Figure 1:
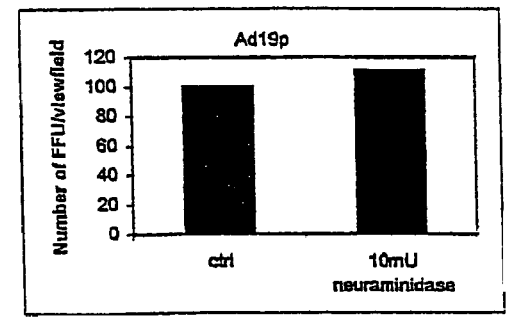
Figure 1:
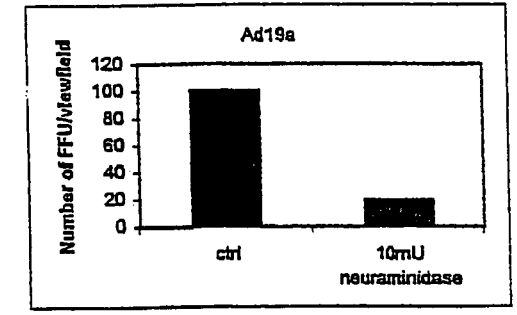
Figure 1:
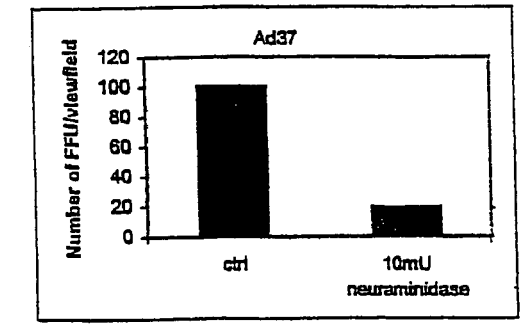

This application is a division of application Ser. No. 10/130,979, now abandoned, filed on May 24, 2002. application Ser. No. 10/130,979 is the national phase of PCT International Application No. PCT/SE00/02313 filed on Nov. 23, 2000 under 35 U.S.C. §371, which claims priority to foreign application SE9904289-7, filed Nov. 26, 1999. The entire contents of each of the above-identified applications are hereby incorporated by reference.

BACKGROUND OF THE INVENTION

1. Field of the Invention

The present invention concerns the field of adenoviral ocular and genital infections and in particular a composition and method for their treatment and prevention.

2. Description of the Related Art

Adenoviruses belong to the group of polyhedral DNA-viruses and are characterised by their icosahedral capsid shell with 20 identical faces and an overall hexagonal shape. In adenoviruses, the capsid is naked, meaning that it does not have the lipid membrane envelope common to many other viruses. This fact may partly explain its resistance to most disinfecting agents and its ability to withstand desiccation.

Adenoviruses afflicting man exhibit 51 different serotypes, which can be divided in six groups depending on the different symptoms. The tropism of the six subgenera A through F is suggested to be directed by differences in the structure of the adenovirus fibre. The adenovirus fibre has specificity for the cellular coxsackie adenovirus receptor (CAR), which is also called the first step receptor. It was therefor surprising when it was demonstrated that representative adenoviruses of subgenus A, C, D, E and F all were demonstrated to bind to CAR.

In a virus particle it is the hexon, penton bases and fibres which initially interact with a susceptible cell. The capsid proteins also interact with the immune system of the infected host. Adenoviruses bind to the first step receptor through the distal part of the fibre—the fibre knob. The charge of this globular structure—having 174-191 amino acid residues—varies between 4.5 to 9.1 in their isoelectric points.

The internalisation step probably involves a second receptor-ligand interaction. The ligand is the variable portion of the adenovirus vertex capsomer and the receptor on the host cell is alpha-v-integrin heterodimers.

Group D is known to cause genital and ocular infections, the latter either engaging the conjunctiva (conjunctivitis) or, in more severe infections, engaging also the cornea (keratoconjunctivitis). Adenoviral ocular infections are known to occur world-wide in community- and office-based epidemics. The main routes of transmission are believed to be direct contact eye-to-hand-to-eye or secondary eye-to-hand-to-hand-to-eye. Also sexual transmission occurs. Other sources of infection are believed to be swimming pools, eye clinics or ophthalmology departments.

Obviously densely populated areas are more prone to epidemic spread of diseases and consequently several epidemics have been observed in Asian countries during the last decade. Terminating established epidemics can be difficult. There are examples of eye clinic or ophthalmology department based epidemics that have taken several months to eradicate completely.

Outbreaks of keratitis are mainly caused by the following adenovirus sero-types; Ad8, Ad19, Ad37 and Ad4, in addition to Herpes virus type 1. On the other hand, conjunctivitis is mainly caused by Ad3, Ad4 and Ad7, but also by Enterovirus 70 and by other adenoviruses.

Antiviral compounds have been developed for the treatment of ocular infections, where Herpes viruses are the causative agent or agents. Attempts to treat adenoviral ocular infections with topical antiherpetic antivirals have been unsuccessful. Therefore the presently applied therapy aims at alleviating the symptoms and limiting the spread of the disease. Alleviating treatments include cold compresses, dark glasses, vasoconstrictors and, although not generally accepted, cyclosporin A and corticosteroids. The use of antibiotics and corticosteroids, either separately or in combination, has not been proven to be effective and, furthermore, is associated with the risk of possible side-effects.

For an overview of adenovirus associated ocular infections, see Gordon et al., Adenovirus Keratoconjunctivitis, in *Ocular Infection and Immunology*, Ed, J. S. Pepsose Mosby, 1996, pages 877-894.

PRIOR ART

It is known that heparin or heparin salts can be used for prophylaxis and therapy of allergic conjunctivitis (DE 195 47 972 A1). In this patent application, filed 1995, it is disclosed that heparin promotes lipolysis by activating the Clearing factor and the excretion of lipo-protein lipase from the endothelial cells. Further, the role of heparin in allergic and anaphylactic reactions is discussed. However, no mentioning of the inhibition of viral binding is to be found.

EP 502 550 discloses pharmaceutical preparations comprising colominic acid and partial hydrolysis products of colominic acid for use as an anti-inflammatory drug.

It has also been shown, that MUC1 and other sialoglycoconjugates inhibit adenovirus-mediated gene transfer to epithelial cells (Arcasoy et al., Am J Resp Cell and Molec Biol, 17 (4): 422).

Presently, there is however no clinically effective antiviral that inhibits the many serotypes of adenoviruses that replicate on the ocular surface and genital mucosa and produce clinical disease. As adenoviral ocular infections have proven to be difficult to treat, there is a demand for improved methods and compositions to this end. It is therefore the aim of the present invention to provide an efficient pharmaceutical composition and methods of treatment to fill this need.

SUMMARY OF THE INVENTION

The above aim is fulfilled by the composition and method as disclosed in the attached claims. The present composition has surprisingly been found to prevent viral binding to ocular cells and the results have been confirmed for several types of adenoviruses.

BRIEF DESCRIPTION OF THE DRAWING FIGURES

Figure 2:
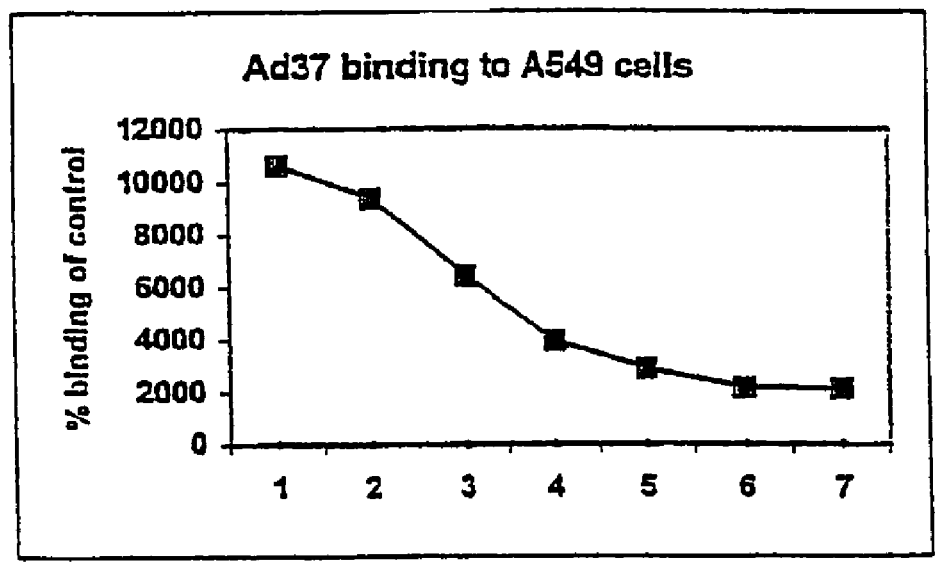
Figure 2:
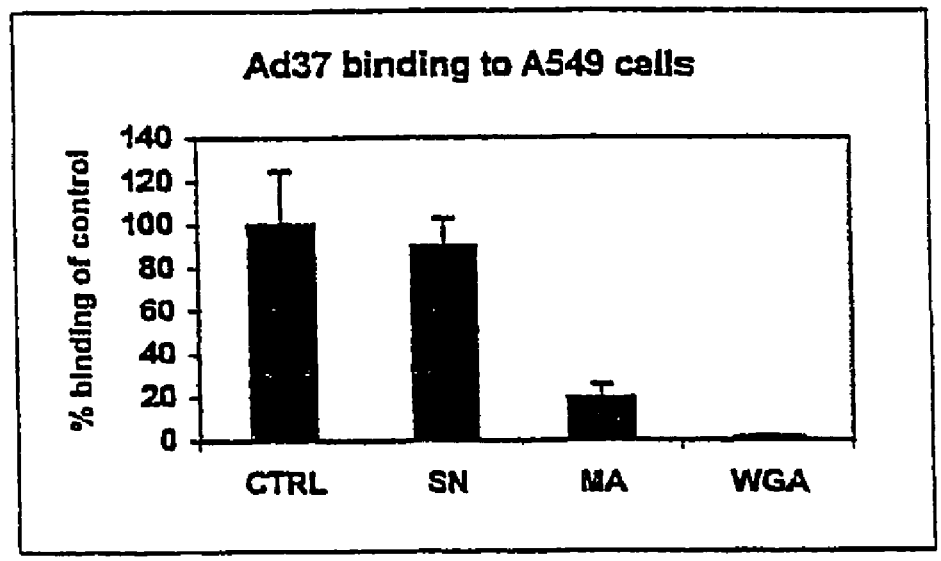
Figure 3:
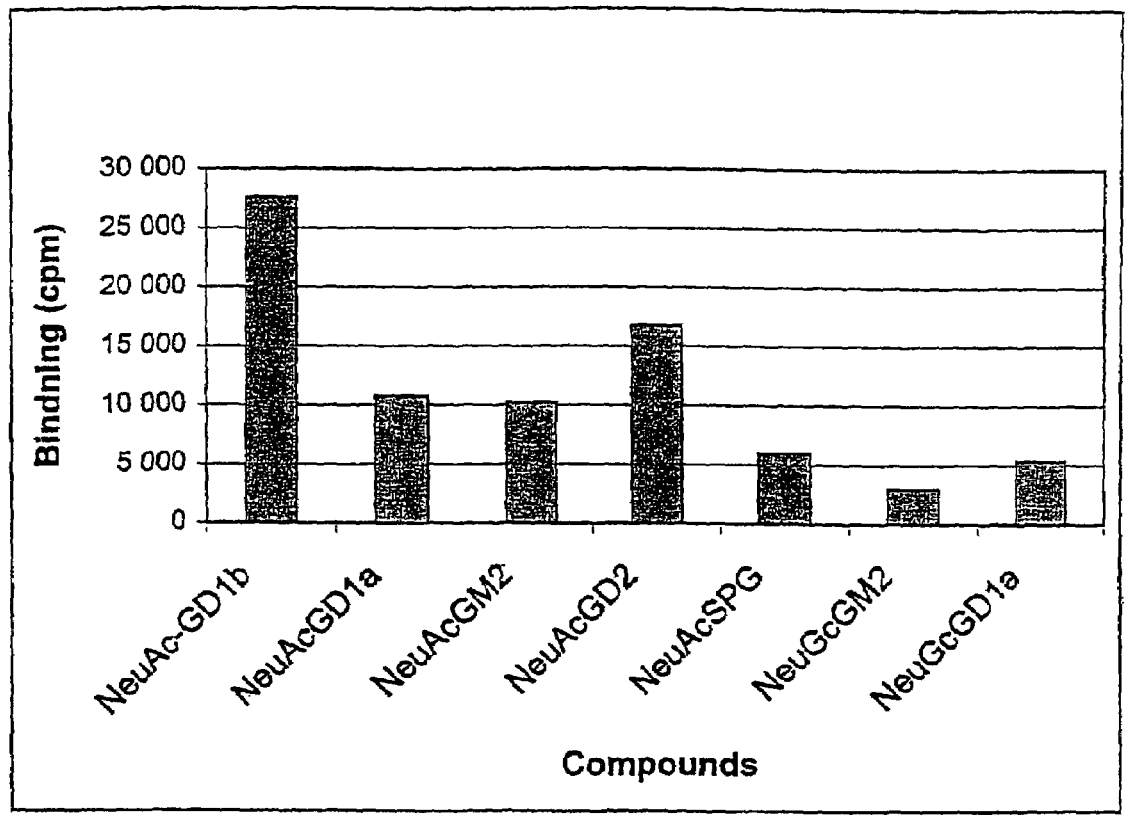

The present invention will be described in closer detail in the following description with reference to the enclosed examples and drawing, in which FIG. 1 shows that certain adenoviruses are dependent on sialic acid to infect human epithelial A549 cells by treatment with neuramidase (FIG. 1A—Ad8; FIG. 1B.—Ad9; FIG. 1C—Ad19p; FIG. 1D—Ad19a; FIG. 1E—Ad37);

FIG. 2 shows that: A) Ad37 binding to A549 cells is inhibited by pre-treatment of the cells with neuramidase specific for (2-3) linked sialic acids and B) Ad37 binding to A544 cells is inhibited by pre-incubation of the cells with a) the lectin wheat germ agglutininn (WGA), binding both (2-3) and (2-6) linked sialic acid and b) the lectin *Maackia amurensis* (MA) specific for (2-3) linked sialic acids, but not by the lectin *Sambucus nigra,* which is specific for (2-6) linked sialic acid; and FIG. 3 shows the binding of $^{125}$I-labeled Ad37 to glycosphingolipids in microtiter wells.

DETAILED DESCRIPTION OF THE PREFERED EMBODIMENTS

The present inventors have surprisingly found that the binding of epidemic kerato-conjunctivitis (EKC)-causing adenoviruses can be inhibited by interfering with their binding to sialic acid. This is based on the finding, that sialic acid appears to be the first step receptor for EKC-causing adenoviruses. In order to block the binding of the viruses to the conjunctiva, corneal and genital epithelial cells, a therapeutically effective amount of a substance, which interferes with the interaction between the virus and the sialic acid receptor, is administered to the site of infection.

The present invention thus concerns pharmaceutical composition for the treatment of adenoviral infections, in particular ocular and genital adenoviral infections, characterized in that said composition comprises a substance interfering with the interaction between the virus and the sialic acid receptor, said substance being present in a therapeutically effective amount. The substance interfering with the interaction between the virus and the sialic acid receptor is chosen among acidic molecules and negatively charged molecules, and in particular sialylated saccharides, their analogues and derivatives thereof and glycosamino glycans, such as heparin and heparan sulphates, their analogues and derivatives thereof.

Preferably the substance interfering with the interaction between the virus and the sialic acid receptor is chosen from the group comprising sialic acid, dextran sulphate, heparin, heparan sulphate, N-glycolyl neuraminic acid, N-acetyl neuraminic acid, colominic acid, 3'N-acetyl neuraminyl N-acetyl lactosamine, N-acetyl neuraminyl-3-fucosyl lactose, N-acetyl neuraminyl lactose, mucin, orosomucoid, mixtures or derivatives thereof.

According to a preferred embodiment of the present invention, the pharmaceutical composition comprises a therapeutically effective amount of sialic acid as the substance interfering with the interaction between the virus and the sialic acid receptor.

According to another embodiment, the substance interfering with the interaction between the virus and the sialic acid receptor is chosen from the group consisting of 3'N-acetyl neuraminyl N-acetyl lactosamine, N-acetyl neuraminyl-3-fucosyl lactose, N-acetyl neuraminyl lactose, colominic acid and mixtures or derivatives thereof.

According to another embodiment the substance interfering with the interaction between the virus and the sialic acid receptor is chosen among dextran sulphate, and glycosamino glycans, such as heparin and heparan sulphates.

According to another embodiment, the substance interfering with the interaction between the virus and the sialic acid receptor is a negatively charged glycoprotein, such as mucin or orosomucoid, preferably mucin.

The pharmaceutical composition is formulated as a gel, a liquid or a paste or contained in a slow-release product, shaped and adapted for insertion under the eyelid or in the vagina. For application in the eye, it is preferred if the composition is clear, in order to affect the field of vision as little as possible. The pharmaceutical composition according to the present invention can comprise other therapeutically effective substances.

The composition can further comprise suitable carriers and adjuvants, normally encountered in the field of ocular and genital medicine, such as cetrimid, aq. ster., carbomer, dilute sodium hydroxide, Vaseline etc.

Generally, the present invention concerns the use of a sialic acid receptor blocking for the manufacture of a pharmaceutical composition for the treatment of adenoviral infections.

In particular, the invention concerns the use of a compound for the manufacture of a pharmaceutical composition for the treatment of adenoviral infections and in particular keratoconjunctivitis, said compound being selected from the group consisting of sialic acid, dextran sulphate, heparin, heparan sulphate, N-glycolyl neuraminic acid, N-acetyl neuraminic acid, colominic acid, 3'N-acetyl neuraminyl N-acetyl lactosamine, N-acetyl neuraminyl-3-fucosyl lactose, N-acetyl neuraminyl lactose, mucin, orosomucoid and mixtures or derivatives thereof.

In particular, the invention concerns the use of any one of the following; colominic acid, 3'N-acetyl neuraminyl N-acetyl lactosamine, N-acetyl neuraminyl-3-fucosyl lactose, and N-acetyl neuraminyl lactose, for the manufacture of a pharmaceutical composition for the treatment of adenoviral infections.

Further, the invention also comprises the use of any one of the following; colominic acid, 3'N-acetyl neuraminyl N-acetyl lactosamine, N-acetyl neuraminyl-3-fucosyl lactose, and N-acetyl neuraminyl lactose, for the manufacture of a pharmaceutical composition for the treatment of keratoconjunctivitis and genital adenoviral infections.

Within the scope of the invention lies a method for the treatment of adenoviral infections, in particular ocular and genital adenoviral infections, characterized in that an therapeutically effective amount of a substance, interfering with the interaction between the virus and the sialic acid receptor, is administered topically to the site of infection.

Preferably, the substance interfering with the interaction between the virus and the sialic acid receptor is chosen among sialic acid, dextran sulphate, heparin, heparan sulphate, N-glycolyl neuraminic acid, N-acetyl neuraminic acid, colominic acid, 3'N-acetyl neuraminyl N-acetyl lactosamine, N-acetyl neuraminyl-3-fucosyl lactose, N-acetyl neuraminyl lactose, mucin, orosomucoid or mixtures or derivatives thereof. An therapeutically effective amount of a substance interfering with the interaction between the virus and the sialic acid receptor is administered to the site of infection by means of a gel, liquid, paste or slow-release ocular and genital inserts.

Monovalent analogues of the sialic acid receptor will have to cover most of the twelve fibres at each of the twelve corners of the virus particle to enable efficient blocking of the binding of the virus particle to the host cell receptors. Divalent or multivalent analogues will, by interacting with a few fibres, enable aggregation of numerous virus particles into a lattice. This will hamper or inhibit virus infection with a higher efficiency, i.e. more inhibition per μmole of ligand. In experiments performed by the present inventors, multivalent ligands, i.e. mucin, have been found to be very effective in inhibiting adenoviral adhesion.

It is therefor included as an embodiment of the present invention that multivalent ligands enabling aggregation of virions into a lattice are used as an interfering principle. Effective pharmaceuticals for the treatment of viral infections, in particular adenoviral ocular and genital infections, can thus be produced, based on such ligands.

One embodiment of the present invention thus encompasses a multivalent substance, e.g. comprising a linker, to which at least two, preferably three or several binding groups are attached. Preferably the multivalent substance has 3 to 5 binding groups, connected to one central node or linker. Such compounds can now be synthesised, as the binding structure has been elucidated.

EXAMPLES

Example 1

Interference of the Binding of Ad37

Interference of the binding of adenovirus subtype 37 (Ad37) with the first step cellular receptor was studied using dextran sulphate and glycosaminoglycans, such as heparin and heparan sulphates. It was shown that such negatively charged molecules could impair binding of the virus. Further, it was demonstrated that Ad37 did not bind to CAR, the receptor which has been claimed to be the characteristic receptor of the subgenus D adenoviruses. In fact, Ad37 was shown to bind to Chinese hamster ovary cells that do not express CAR. This binding could be inhibited by neuraminidase specific for (2-3) linked sialic acid but not by neuraminidase for (2-6) linked sialic acid. Furthermore, lectins from *Maackia amurensis* specific for (2-3) linked sialic acid and wheat germ agglutinin binding to all types of sialic acid, blocked the binding. However, *Sambucus nigra* lectin, specific for (2-6) linked sialic acid, failed to block the binding. It was thus confirmed that the cellular receptor for Ad37 is (2-3) linked sialic acid. See FIG. 2.

The results obtained using heparin are presented in table 1.

TABLE 1

Non-specific, charge-dependent inhibition of adenovirus binding to Chang C conjunctival cells with heparin

| Adenovirus type | Concentration of heparin causing 50% inhibition of binding (μM) | Maximal inhibition of binding in % (670 μM heparin) |
| --- | --- | --- |
| 8 | 30 | 92 |
| 19a | 25 | 90 |
| 37 | 20 | 87 |

In an extended study, the adenovirus types Ad8, Ad19a and Ad37, which all are known to cause epidemic keratoconjunctivitis (EKC), were compared to Ad9 and Ad19p which do not cause EKC. Binding to human epithelial A549 cells was investigated. Cellular treatment with 10 units neuramidase (removing sialic acid) significantly inhibited both binding and subsequent infection caused by Ad8, Ad19a and Ad37. This effect was not seen in the controls; Ad9 and Ad19p. This means that Ad8, Ad19a and Ad37, but not types 9 and 19p infect A549 cells by binding to cell surface sialic acid. The results are presented in FIG. 1.

Example 2

Inhibitory Effect of Sialylated Glycoproteins

The effect of glycoproteins to inhibit Ad37 binding to Chang C conjunctival cells was investigated using the following glycoproteins: fetuin, mucin, orosomucoid and glycophorin A. The results are presented in table 2.

TABLE 2

Specific inhibition of Ad37 binding to Chang cells with sialylated glycoproteins

| Glycoprotein type | Concentration of glycoprotein causing 50% inhibition of Ad37 binding (μM) | Maximal inhibition of Ad37 binding in % (500 μM) |
| --- | --- | --- |
| Fetuin | 420 | 62 |
| Mucin | 8 | 89 |
| Orosomucoid | 75 | 77 |
| Glycophorin A | >500 | 45 |

The results show that significant inhibition can be achieved with very low concentrations of glycoprotein, e.g. 8 μM mucin suffices to reach 50% inhibition and a concentration of 500 μM gives a 89% inhibition.

Example 3

The Ability of Different Carbohydrates to Inhibit Ad37 Binding

The inventors confirmed the inventive concept by determining the inhibition achieved with different carbohydrates, using adenovirus type 37 and Chang C conjunctival cells.

It was shown that 160 mmol concentrations of lactose, galactose, mannose or in the form of acetyl galactose amine, acetyl glucose amine, and acetyl mannose amine, did not interfere with the binding of Ad37 to sialic acid expressing cells. However, N-glycolyl neuraminic acid, N-acetyl neuraminic acid, colominic acid, 3'N-acetyl neuraminyl N-acetyl lactosamine, 6'N-acetyl neuraminyl N-acetyl lactosamine, N-acetyl neuraminyl-3-fucosyl lactose, and N-acetyl neuraminyl lactose were all effective in inhibiting binding of Ad37 to sialic acid-expressing cells. The results are presented in table 3.

TABLE 3

Specific inhibition of Ad37 to Chang cells with sialic acid carbohydrates

| Carbohydrate type | Concentration of carbohydrate causing 50% inhibition of Ad37 binding (mM) | Maximal inhibition of Ad37 binding in % (160 mM) |
| --- | --- | --- |
| N-glycolyl-neuraminic acid | 40 | 91 |
| N-acetyl-neuraminic acid | 18 | 82 |
| 3'-N-acetyl-neuraminyl-N-acetyllactosamine | 5 | —* |
| 6'-N-acetyl-neuraminyl-N-acetyllactosamine | 7 | —* |
| N-Acetyl Neuraminyl-3-Fucosyl Lactose | 5 | —* |
| Colominic acid | 8 | 79 |
| N-acetyl-neuraminyllactose | 5 | 95 |

*Not determined

All data are visualised as the dose required for 50% inhibition of adenovirus binding and the maximum inhibition of adenovirus binding.

The results clearly show that significant inhibition can be achieved with very low carbohydrate concentrations. Notably, 3'N-acetyl neuraminyl N-acetyl lactosamine, 6'N-acetyl neuraminyl N-acetyl lactosamine, N-acetyl neuraminyl-3-fucosyl lactose, N-acetyl neuraminyl lactose, and colominic acid caused a 50% inhibition in doses less than 10 mM.

Further, almost total inhibition was achieved with a 160 mM concentration of specific carbohydrates, in particular with N-acetyl neuraminyl lactose.

Further carbohydrate candidates which have not yet been tested include 2-O-methyl-α-β-N-acetyl neuraminic acid and N-acetyl neuraminic acid methyl ester.

N-glycolyl-neuraminic acid and N-acetyl-neuraminic acid are monoscharides. N-acetyl-neuraminyl-fucosyl-lactose has the formula α-Neu-5-Ac-(2-3)-β-D-Gal(1-4)-(α-Fuc-(1-3))-Glc. 3'-N-acetyl-neuraminyl-N-acetyl-lactoseamine has the formula α-NeuNAc-(2-3)-β-D-Gal-(1-4)-D-GlcNAc. 6'-N-acetyl-neuraminyl-N-acetyl-lactoseamine has the formula α-Neu-5Ac-(2-6)-β-D-Gal-(1-4)-D-GlcNAc. N-acetyl-neuraminyl-lactose is a mixture of α-Neu-5Ac-(2-3)-β-D-Gal-(1-4)-D-Glc and α-Neu-5Ac-(2-6)-β-D-Gal-(1-4)-D-Glc.

Preliminary results from thin layer chromatography shown in FIG. 3 indicate, that the following structures are effective for Ad37 virus binding:

α-NeuAc-(2-3)-β-D-Gal-(1-3)-β-GalNAc
NeuAc-GD1b or Galβ3GalNAcβ4(NeuAcα8NeuAcα3)Galβ4Glcβ1
NeuAc-GD1a or NeuAcα3Galβ3GalNAcβ4(NeuAcα3)Galβ4Glcβ1
NeuAcGM2 or GalNAcβ4(NeuAcα3)Galβ4Glcβ1
NeuAc-GD2 or GalNAcβ4(NeuAcα8NeuAcα3)Galβ4Glcβ1

Using this information, pharmaceutical compositions for interfering with the interaction between a virus and the sialic acid receptor can be developed. In particular, multivalent substances, capable of interacting with several virus particles causing aggregation of viruses, can be constructed based on the above structure.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

The invention claimed is:

1. A method for treating an adenoviral infection in a patient, comprising: topically administering to said patient in need thereof, an effective amount of a composition for topical administration to the ocular or genital areas of said patient, said composition comprising a substance selected from the group consisting of sialic acid, N-glycolyl neuraminic acid, N-acetyl neuraminic acid, colominic acid, 3'N-acetyl neuraminyl N-acetyl lactosamine, 6'N-acetyl neuraminyl N-acetyl lactosamine, N-acetyl neuraminyl-3-fucosyl lactose, N-acetyl neuraminyl lactose, and mixtures thereof, said substance being present in a therapeutically effective amount.

2. The method according to claim 1, wherein said substance is selected from the group consisting of 3'N-acetyl neuraminyl N-acetyl lactosamine, 6'N-acetyl neuraminyl N-acetyl lactosamine, N-acetyl neuraminyl-3-fucosyl lactose, N-acetyl neuraminyl lactose, and colominic acid.

3. A method for treating an adenoviral infection in a patient, comprising:
topically administering to said patient in need thereof an effective amount of a composition for topical administration to the ocular or genital area of said patient, said composition comprising a multivalent substance that aggregates virus particles into a lattice and comprises a linker to which at least two binding groups, selected from sialic acid, N-glycolyl neuraminic acid, N-acetyl neuraminic acid, colominic acid, 3'N-acetyl neuraminyl N-acetyl lactosamine, N-acetyl neuraminyl-3-fucosyl lactose, N-acetyl neuraminyl lactose, are attached, said substance being present in a therapeutically effective amount, and wherein said multivalent substance is not mucin.

4. The method according to claim 1, wherein said patient suffers from keratoconjunctivitis.

5. A method for treating an adenoviral infection in a patient, comprising:
administering to said patient in need thereof, an effective amount of a composition comprising a substance selected from the group consisting of sialic acid, N-glycolyl neuraminic acid, N-acetyl neuraminic acid, colominic acid, 3'N-acetyl neuraminyl N-acetyl lactosamine, 6'N-acetyl neuraminyl N-acetyl lactosamine, N-acetyl neuraminyl-3-fucosyl lactose, N-acetyl neuraminyl lactose, and mixtures thereof, said substance being present in a therapeutically effective amount.

6. The method according to claim 5, wherein said substance is selected from the group consisting of 3'N-acetyl neuraminyl N-acetyl lactosamine, 6'N-acetyl neuraminyl N-acetyl lactosamine, N-acetyl neuraminyl-3-fucosyl lactose, N-acetyl neuraminyl lactose, and colominic acid.

7. A method for treating an adenoviral infection in a patient, comprising:
topically administering to said patient in need thereof an effective amount of a composition a multivalent substance that aggregates virus particles into a lattice and comprises a linker to which at least two binding groups, selected from sialic acid, N-glycolyl neuraminic acid, N-acetyl neuraminic acid, colominic acid, 3'N-acetyl neuraminyl N-acetyl lactosamine, N-acetyl neuraminyl-3-fucosyl lactose, N-acetyl neuraminyl lactose, are attached, said substance being present in a therapeutically effective amount, and wherein said multivalent substance is not mucin.

8. The method according to claim 7, further comprising topically administering said composition to said patient.

9. The method according to claim 5, wherein said patient suffers from keratoconjunctivitis.

10. A method for treating keratoconjunctivitis in a patient, comprising:
topically administering to the ocular area of said patient in need thereof, an effective amount of a composition comprising a substance selected from the group consisting of sialic acid, N-glycolyl neuraminic acid, N-acetyl neuraminic acid, colominic acid, 3'N-acetyl neuraminyl N-acetyl lactosamine, 6'N-acetyl neuraminyl N-acetyl lactosamine, N-acetyl neuraminyl-3-fucosyl lactose, N-acetyl neuraminyl lactose, and mixtures thereof, said substance being present in a therapeutically effective amount.

11. The method according to claim 10, wherein said substance is selected from the group consisting of 3'N-acetyl neuraminyl N-acetyl lactosamine, 6'N-acetyl neuraminyl N-acetyl lactosamine, N-acetyl neuraminyl-3-fucosyl lactose, N-acetyl neuraminyl lactose, and colominic acid.

12. A method for treating keratoconjunctivitis in a patient, comprising:
topically administering to the ocular or genital area of said patient in need thereof, an effective amount of a composition comprising a multivalent substance that aggregates virus particles into a lattice and comprises a linker to which at least two binding groups, selected from sialic acid, N-glycolyl neuraminic acid, N-acetyl neuraminic acid, colominic acid, 3'N-acetyl neuraminyl N-acetyl lactosamine, N-acetyl neuraminyl-3-fucosyl lactose, N-acetyl neuraminyl lactose, are attached, said substance being present in a therapeutically effective amount and wherein said multivalent substance is not mucin.

13. A method for inhibiting adenoviral binding to cells in a patient, comprising:

topically administering to said patient in need thereof, an effective amount of a composition for topical administration to the ocular or genital areas of said patient, said composition comprising a substance selected from the group consisting of sialic acid, N-glycolyl neuraminic acid, N-acetyl neuraminic acid, colominic acid, 3'N-acetyl neuraminyl N-acetyl lactosamine, 6'N-acetyl neuraminyl N-acetyl lactosamine, N-acetyl neuraminyl-3-fucosyl lactose, N-acetyl neuraminyl lactose, and mixtures thereof, said substance being present in a therapeutically effective amount, wherein the compound is administered to the site of infection.

14. The method according to claim 13, wherein said substance is selected from the group consisting of 3'N-acetyl neuraminyl N-acetyl lactosamine, 6'N-acetyl neuraminyl N-acetyl lactosamine, N-acetyl neuraminyl-3-fucosyl lactose, N-acetyl neuraminyl lactose, and colominic acid.

15. A method for inhibiting adenoviral binding to cells in a patient, comprising:

administering to said patient in need thereof, an effective amount of a composition comprising a substance selected from the group consisting of sialic acid, N-glycolyl neuraminic acid, N-acetyl neuraminic acid, colominic acid, 3'N-acetyl neuraminyl N-acetyl lactosamine, 6'N-acetyl neuraminyl N-acetyl lactosamine, N-acetyl neuraminyl-3-fucosyl lactose, N-acetyl neuraminyl lactose, and mixtures thereof, said substance being present in a therapeutically effective amount, wherein the compound is administered to the site of infection.

16. The method according to claim 15, wherein said substance is selected from the group consisting of 3'N-acetyl neuraminyl N-acetyl lactosamine, 6'N-acetyl neuraminyl N-acetyl lactosamine, N-acetyl neuraminyl-3-fucosyl lactose, N-acetyl neuraminyl lactose, and colominic acid.

17. A method for inhibiting adenoviral binding to cells in a patient, comprising topically administering to the ocular area of said patient in need thereof, an effective amount of a composition comprising a substance selected from the group consisting of sialic acid, N-glycolyl neuraminic acid, N-acetyl neuraminic acid, colominic acid, 3'N-acetyl neuraminyl N-acetyl lactosamine, 6'N-acetyl neuraminyl N-acetyl lactosamine, N-acetyl neuraminyl-3-fucosyl lactose, N-acetyl neuraminyl lactose, and mixtures thereof, said substance being present in a therapeutically effective amount, wherein the compound is administered to the site of infection.

18. The method according to claim 17, wherein said substance is selected from the group consisting of 3'N-acetyl neuraminyl N-acetyl lactosamine, 6'N-acetyl neuraminyl N-acetyl lactosamine, N-acetyl neuraminyl-3-fucosyl lactose, N-acetyl neuraminyl lactose, and colominic acid.

* * * * *